US007691104B2

(12) United States Patent
Yamamoto et al.

(10) Patent No.: US 7,691,104 B2
(45) Date of Patent: Apr. 6, 2010

(54) ENDOSCOPIC TREATMENT TOOL

(75) Inventors: Hironori Yamamoto, Shimotsuke (JP);
Megumi Kimura, Tokyo (JP); Ichiro Takahashi, Toyko (JP); Ryoko Yamazaki, Kuroishi (JP); Tatsuya Kaneko, Tokyo (JP)

(73) Assignees: Olympus Medical Systems Corporation, Tokyo (JP); SRJ Corporation, Tokyo (JP)

( * ) Notice: Subject to any disclaimer, the term of this patent is extended or adjusted under 35 U.S.C. 154(b) by 418 days.

(21) Appl. No.: 11/880,995

(22) Filed: Jul. 25, 2007

(65) Prior Publication Data
US 2009/0030272 A1 Jan. 29, 2009

(51) Int. Cl.
*A61B 18/18* (2006.01)
(52) U.S. Cl. .............................. 606/47; 606/51; 606/52
(58) Field of Classification Search ............. 606/46–47, 606/51–52, 205–208; 600/562, 105–106
See application file for complete search history.

(56) References Cited

U.S. PATENT DOCUMENTS

| 4,011,872 | A | * | 3/1977 | Komiya ........................ 606/47 |
| 4,418,692 | A | | 12/1983 | Guay |
| 5,667,525 | A | * | 9/1997 | Ishibashi .................... 606/206 |
| 6,273,887 | B1 | | 8/2001 | Yamauchi et al. |
| 2004/0054387 | A1 | | 3/2004 | Nakada et al. |
| 2007/0021749 | A1 | * | 1/2007 | Suzuki et al. ................. 606/47 |
| 2007/0135813 | A1 | * | 6/2007 | Yamamoto et al. ............ 606/46 |
| 2008/0009856 | A1 | * | 1/2008 | Suzuki ........................ 606/46 |
| 2008/0200756 | A1 | * | 8/2008 | Okada et al. ................. 600/106 |

FOREIGN PATENT DOCUMENTS

| EP | 1 350 480 A1 | 10/2003 |
| EP | 1 782 742 A2 | 5/2007 |
| JP | S58-13213 | 1/1983 |
| JP | 05-042167 | 2/1993 |
| JP | 8-299355 | 11/1996 |
| JP | 2000-70280 | 3/2000 |
| JP | 2002-113015 | 4/2002 |
| JP | 2004-337422 | 12/2004 |
| JP | 2007-117405 | 5/2007 |

\* cited by examiner

*Primary Examiner*—Linda C Dvorak
*Assistant Examiner*—Benjamin Lee
(74) *Attorney, Agent, or Firm*—Scully, Scott, Murphy & Presser, P.C.

(57) ABSTRACT

An endoscopic treatment tool is provided which includes: a grasping portion that has a first shoulder portion and second shoulder portion; a current-carrying portion that protrudes out from a distal end of each of the first and second shoulder portions; a pivot portion that is disposed in the distal end of the first shoulder portion so as to protrude in substantially the same direction as the longitudinal direction of the first shoulder portion, the distal end of the pivot portion being provided with an insulating portion; a wire that is connected to the grasping portion; a sheath which has a tubular shape, and into which the wire and grasping portion are inserted; a main body to which the sheath is fixed; and a sliding portion which is disposed to move in the longitudinal direction of the main body in a sliding manner, and to which the wire is connected.

4 Claims, 7 Drawing Sheets

ENDOSCOPIC TREATMENT TOOL

BACKGROUND OF THE INVENTION

1. Field of the Invention

The present invention relates to an endoscopic treatment tool that is used by being inserted into body cavities in a transendoscopic manner and being supplied with high-frequency current.

2. Description of Related Art

In the past, for the purpose of incision of polyps or the like, there have been known endoscopic treatment tools in which high-frequency current is supplied to a grasping portion having bifurcated distal ends. In the grasping portion of the treatment tools, the bifurcated distal ends are configured to have the same lengths in order to completely remove target tissues by high-frequency treatment (see JP-A-5-42167, for example).

In order to completely remove target tissues such as polyps, it is necessary to control the direction of the grasping portion so that the base of the tissue is disposed between the bifurcated distal ends. The treatment tool is used by being inserted into a channel provided along a scope of an endoscope. Operators such as a physician usually operate the scope, not the treatment tool. Therefore, when operators manually locate the grasping portion, the operators move one of the distal ends of the grasping portion to press against a tissue adjacent to the target tissue and rotate the scope itself about the one distal end.

However, there are many irregularities around the tissue such as polyps. In the case of the treatment tool disclosed in JP-A-5-42167, even a trial to move the one distal end of the grasping portion to press against the adjacent tissue may result in the other distal end making simultaneous contact with the adjacent tissue. In this case, it becomes difficult or impossible to rotate the grasping portion, thereby causing problems in locating the grasping portion.

SUMMARY OF THE INVENTION

According to some aspects of the invention, there is provided an endoscopic treatment tool which includes: a grasping portion that has a first shoulder portion and a second shoulder portion having substantially the same length as that of the first shoulder portion, the first and second portions being arranged to make a predetermined angle relative to each other; a current-carrying portion that protrudes out from a distal end of each of the first and second shoulder portions; a pivot portion that is disposed in the distal end of the first shoulder portion so as to protrude in substantially the same direction as the longitudinal direction of the first shoulder portion, the distal end of the pivot portion being provided with an insulating portion; a wire in which a first end portion thereof is connected to the grasping portion; a sheath which has a tubular shape, and into which the wire and the grasping portion are inserted in a sliding manner; a main body to which the sheath is fixed; and a sliding portion which is disposed to move in the longitudinal direction of the main body in a sliding manner, and to which is connected a second end portion of the wire.

BRIEF DESCRIPTION OF THE DRAWINGS

The above and other features and advantages of the present invention will become more apparent by describing in detail exemplary embodiments thereof with reference to the attached drawings in which.

DESCRIPTION OF EXEMPLARY EMBODIMENTS

First Embodiment

Hereinafter, an endoscopic treatment tool in accordance with a first embodiment of the present invention will be described with reference to FIG. 1.

Figure 1:
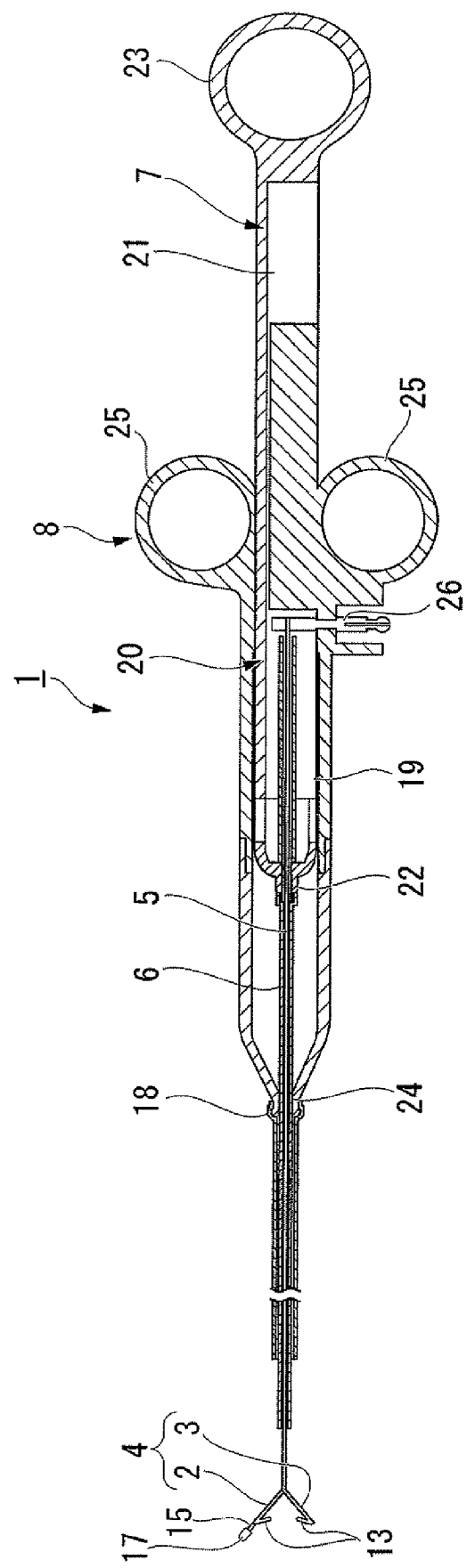
FIG. 1 is a diagram showing an endoscopic treatment tool in accordance with a first embodiment of the present invention.

As shown in FIG. 1, the endoscopic treatment tool 1 of the present embodiment is a treatment tool that is used by being supplied with high-frequency current. The endoscopic treatment tool 1 is configured to include: a grasping portion 4 having a first shoulder portion 2 and a second shoulder portion 3; a wire 5 in which a first end portion thereof is connected to a proximal end of the grasping portion 4; a first sheath 6 which has a tubular shape, and into which the wire 5 and the grasping portion 4 are inserted in a sliding manner; a main body 7 to which the first sheath 6 is fixed; and a sliding portion 8 which is disposed to move along the main body 7 in a sliding manner, and to which is connected a second end portion of the wire 5.

Figure 2:
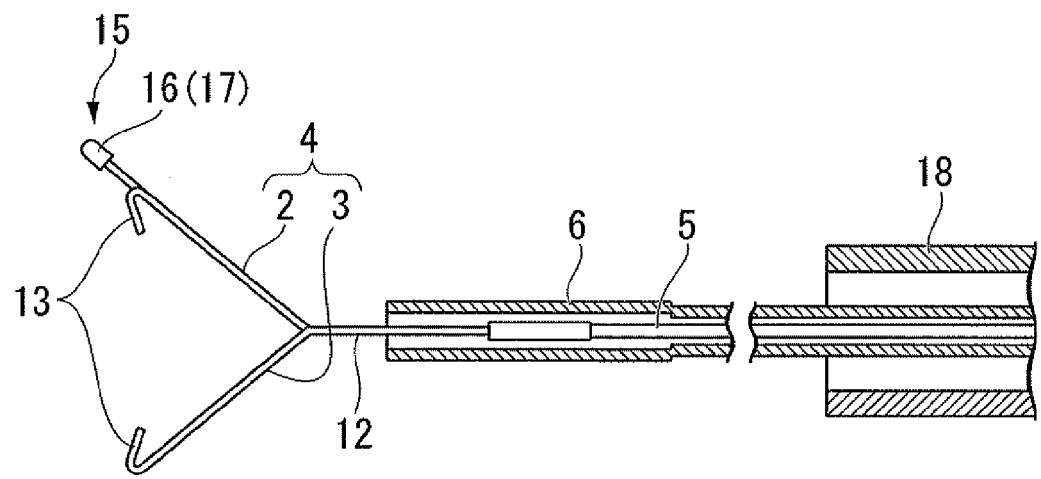
FIG. 2 is an enlarged view of a grasping portion of the endoscopic treatment tool of the first embodiment.
Figure 3:
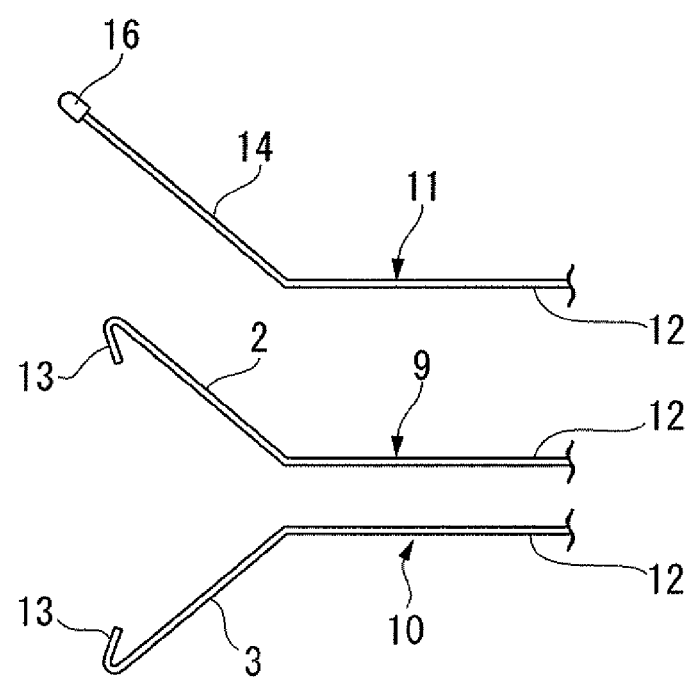
FIG. 3 is an enlarged exploded view of the grasping portion.

FIG. 2 is an enlarged view of the grasping portion 4, and FIG. 3 is an enlarged exploded view of the grasping portion 4. As shown in FIG. 3, the grasping portion 4 includes a first grasping member 9, a second grasping member 10, and a third grasping member 11, which are formed of a rod-shaped metallic material. The first grasping member 9 and the second grasping member 10 are bent at predetermined positions so that the first and second shoulder portions 2 and 3 have substantially the same lengths. As shown in FIG. 2, the first grasping member 9 and the second grasping member 10 are arranged such that the first and second shoulder portions 2 and 3 make a predetermined angle, for example, 80 degrees relative to each other. Proximal portions 12 of the first and second grasping members 9 and 10 are fixed by means of soldering or the like. The proximal portions 12 are connected to the first end portion of the wire 5.

The distal ends of the first and second shoulder portions 2 and 3 are folded back so as to protrude on a plane defined by the shoulder portions 2 and 3, thereby forming current-carrying portions 13. The current-carrying portions 13 are supplied with high-frequency current, which will be described later, and are used to cauterize target tissues such as polyps.

The third grasping member 11 is bent at a predetermined position and includes a third shoulder portion 14. As shown in FIG. 3, the third shoulder portion 14 is longer than the first shoulder portion 2 by a predetermined length (about 3 mm, for example). The third grasping member 11 is integrally formed with the first grasping member 9 by fixing the third shoulder portion 14 to the first shoulder portion 2 by means of soldering or the like. The distal end of the third shoulder portion 14 protrudes further out from the distal end of the first shoulder portion 2 in substantially the same direction as the longitudinal direction of the first shoulder portion 2. The distal end of the third shoulder portion 14 serves as a pivot portion 15.

The distal end of the pivot portion 15 is capped with a cap 16 formed of an insulating material such as silicon rubber. Therefore, the distal end of the pivot portion 15 can be rounded by the cap 16. In addition, the cap 16 provides insulation to the pivot portion 15 and thus serves as an insulating portion 17.

The first sheath 6 is formed in a tubular shape and made of resin such as tetrafluoroethylene (PTFE), and the wire 5 can be inserted into the first sheath 6. In addition, the first sheath 6 is inserted into a second sheath (an outer sheath) 18 that is formed in a tubular shape and made of resin such as polyethylene. The length of the second sheath 18 is set substantially identical to the length of the operation channel of an endoscope device into which the endoscopic treatment tool 1 is to be inserted.

The main body 7 is a rod-shaped member made of resin or the like. As shown in FIG. 1, the main body 7 includes a reception portion 20 having a reception groove 19 for receiving the first sheath 6 and the wire 5 therein, and an operating portion 21 extending from the reception portion 20.

The reception groove 19 is formed with a predetermined width and extends in the longitudinal direction of the main body 7 so as to include the central axial line of the reception portion 20. A through-hole 22 is formed at the center of the distal end of the reception portion 20 so as to communicate with the reception groove 19. The first sheath 6 and the wire 5 are received in the reception groove 19 via the through-hole 22, and the first sheath 6 is welded and fixed to the distal end of the reception portion 20. That is, the first sheath 6 and the main body 7 are integrally formed with each other, and the wire 5 and the grasping portion 4 are inserted into the first sheath 6 so as to move toward and away from the first sheath 6 in a sliding manner. A first annular handle 23 is provided at the end of the operating portion 21.

The sliding portion 8 is formed of resin or the like and substantially in a cylindrical shape so as to surround the main body 7. A through-hole 24 is formed in the distal end of the sliding portion 8 so as to allow the first sheath 6 to be inserted therein. The end of the second sheath 18 is welded and fixed to the distal end of the sliding portion 8.

A pair of second annular handles 25 are provided on the outer surface (on the upper and lower sides of FIG. 1) of the sliding portion 8. A wire fixing plug 26 formed of a conductor such as metal is provided on the side surface of the sliding portion 8 closer to the grasping portion 4 side than the second handles 25 so as to protrude toward the inside of the reception groove 19.

The wire fixing plug 26 is connected and fixed to the second end portion of the wire 5 that have passed through the first sheath 6 in the inside of the reception groove 19. That is, the sliding portion 8 is connected to the second sheath 18 and the wire 5. The sliding portion 8 is disposed such that the sliding portion 8 can move in the longitudinal direction of the main body 7 in a sliding manner by the wire fixing plug 26 moving in the inside of the reception groove 19.

The wire fixing plug 26 is connected to a high-frequency current source (not shown) so that high-frequency current can be supplied to the current-carrying portions 13 via the wire 5.

Next, the operations of the endoscopic treatment tool 1 having such a configuration will be described with reference to FIGS. 4A to 4D. The following description is directed to the incision of polyps using the endoscopic treatment tool 1.

Figure 4A:
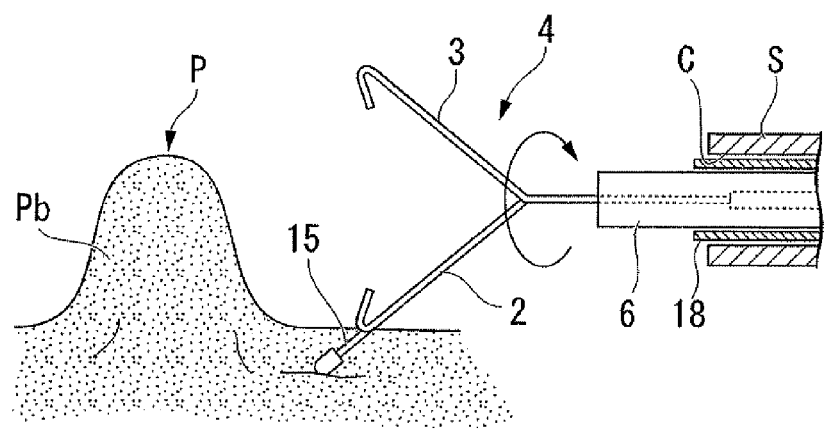
FIGS. 4A to 4D are diagrams showing the operation of the grasping portion at the time of using the endoscopic treatment tool.

First, the grasping portion 4 is moved to the vicinity of a polyp P in accordance with a known procedure. Specifically, the second sheath 18 is inserted into a channel C provided in the scope of a endoscope device S in the state in which the grasping portion 4 is received in the first sheath 6. Next, as shown in FIG. 4A, the second sheath 18 is made to protrude slightly from the distal end of the channel C. Thereafter, the first sheath 6 having the grasping portion 4 received therein is made to protrude from the distal end of the second sheath 18. Here, from the viewpoint of a locating operation to be described later, the protruding length of the first sheath 6 is preferably about 2 cm. When the grasping portion 4 is moved close to the polyp P while observing the polyp P to be treated using the scope of the endoscope device S, and the main body 7 is pulled so as to separate the first handle 23 and the second handle 25 away from each other, the first sheath 6 fixed to the main body 7 is made to be retracted toward the inside of the second sheath 18, and the grasping portion 4 is exposed in the state in which the first shoulder portion 2 and the second shoulder portion 3 are bifurcated to make a predetermined angle.

In this state, the endoscope device S is operated to move the pivot portion 15 of the first shoulder portion 2 to press against a tissue in front of the polyp P. Then, the endoscope device S is rotated in the arrow direction about the pivot portion 15 such that a polyp base Pb is disposed between the first shoulder portion 2 and the second shoulder portion 3, thereby locating the grasping portion 4.

Figure 4B:
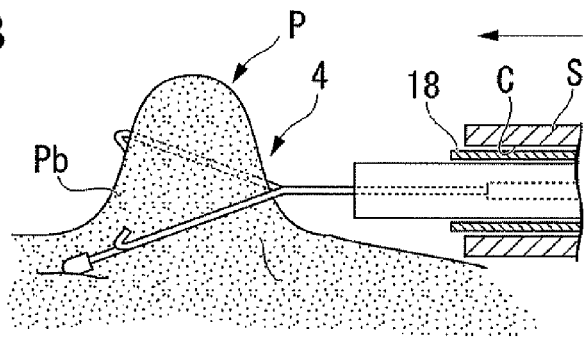

As shown in FIG. 4B, when the grasping portion 4 is made to move forward so that the polyp base Pb is disposed between the bifurcated distal ends thereof while maintaining the posture of the grasping portion 4, the sliding portion 8 is made to be attracted so as to move the first handle 23 and the second handle 25 close to each other.

Figure 4C:
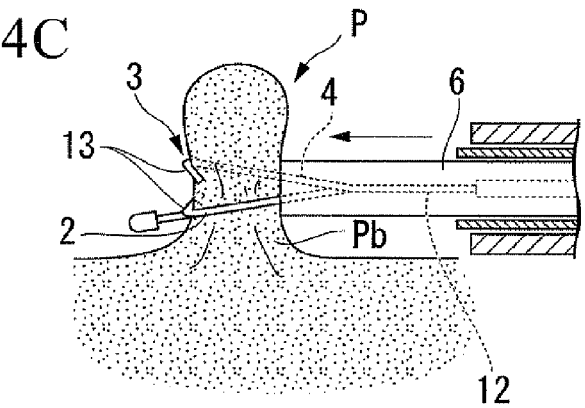

At this time, since the second sheath 18 forms a single body along with the sliding portion 8 and is immovable due to a frictional force produced between the outer side surfaces of the second sheath 18 and the inner side surfaces of the channel C, the sliding portion 8 is not attracted actually. Therefore, the grasping portion 4 is also immovable because the grasping portion 4 is connected to the distal end of the wire 5 fixed to the sliding portion 8. As shown in FIG. 4C, however, by a reaction force against such an operation, the main body 7 and the first sheath 6 are made to move forward and the grasping portion 4 is gradually received in the inside of the first sheath 6 from the side of the proximal end 12.

By the movement of the first sheath 6, the grasping portion 4 is gradually closed to decrease the angle made by the first shoulder portion 2 and the second shoulder portion 3 without changing its positional relationship with the polyp P. In the state in which the polyp base Pb is firmly caught by the grasping portion 4, high-frequency current is supplied to the current-carrying portions 13 from the high-frequency current source (not shown).

Figure 4D:
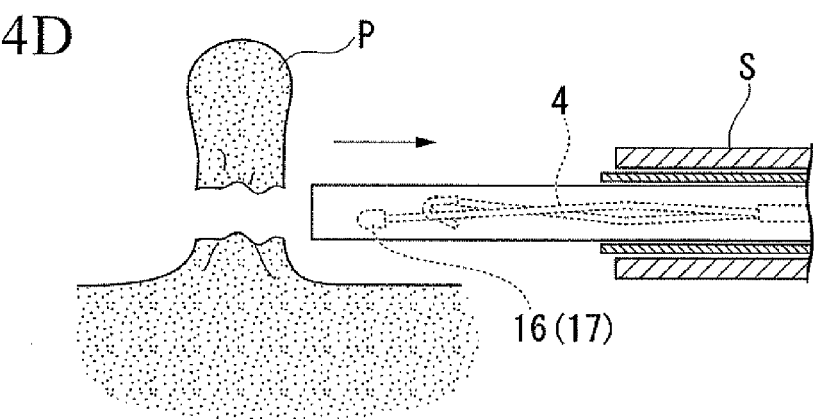

Thereafter, as shown in FIG. 4D, while cauterizing the polyp P by means of the current-carrying portions 13, the sliding portion 8 is pulled forward, whereby the polyp P is cauterized and incised. At this time, since the distal end of the pivot portion 15 is insulated by the cap 16, adjacent tissues in contact with the pivot portion 15 are not damaged by the high-frequency current.

According to the endoscopic treatment tool 1 of the present embodiment, since the pivot portion 15 is provided to the first shoulder portion 2, even when the pivot portion 15 is moved to press against tissues, it is possible to suppress the distal ends of the first and second shoulder portions 2 and 3 from making simultaneous contact with the tissues. Accordingly, it becomes easy to perform the operation of locating the grasping portion 4 which is performed by rotating the grasping portion 4 about the pivot portion 15.

Furthermore, since the insulating portion 17 is provided to the distal end of the pivot portion 15, even when high-frequency current is supplied to the current-carrying portions 13, the portion in contact with the pivot portion 15 is not supplied with the current.

Even when the tissue adjacent to the target tissue such as polyps is in close contact with the target tissue on the back side thereof, by causing the pivot portion 15 to push the adjacent tissue further out toward the back side, it becomes possible to separate the adjacent tissue from the target tissue. Accordingly, it becomes possible to cauterize only the target tissue without causing any damage on the adjacent tissue by the supply of the current.

The second sheath 18 provided on the outer side of the first sheath 6 is fixed in the channel C of the endoscope device S. Therefore, when the sliding portion 8 is made to be attracted in such a manner to close the grasping portion 4 that is similar to the case of a known endoscopic treatment tool, the main body 7 and the first sheath 6 are actually made to move forward by this operation. Accordingly, it becomes possible to close the first shoulder portion 2 and the second shoulder portion 3 without allowing the grasping portion 4 to move, and thus users can perform the treatment in a stable manner.

In addition, the opening and closing of the grasping portion 4 can be performed by the same operation as a known endoscopic treatment tool, and therefore, the users can operate the endoscopic treatment tool without feeling any stress in the operation.

Since the second sheath 18 is disposed between the first sheath 6 and the channel C of the endoscope device S, it is possible to operate the main body 7 and the first sheath 6 in an easy manner as a result of the reduced frictional force applied to the first sheath 6.

The above description has been made to the case in which the pivot portion 15 is moved to press against the tissue in front of the polyp P, thus locating the grasping portion 4, and the grasping portion 4 is made to move forward to the polyp P, thereby cauterizing the polyp P by the supply of the current. However, instead of the above method, the pivot portion 15 may be moved to press against the portion in the polyp base Pb of the tissue, the grasping portion 4 is rotated, thus locating the grasping portion 4, and in this state, the grasping portion 4 is closed, thereby cauterizing the polyp P by the supply of the current.

Second Embodiment

Figure 6:
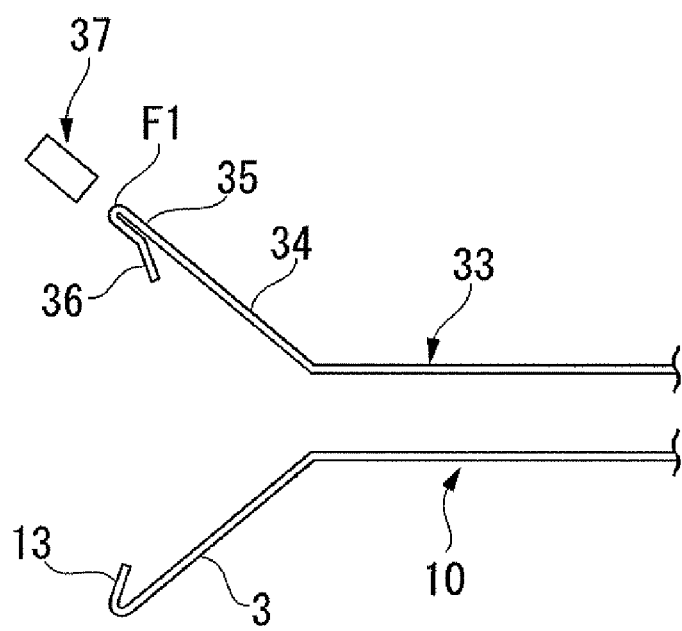
FIG. 6 is an enlarged exploded view of the grasping portion.
Figure 7:
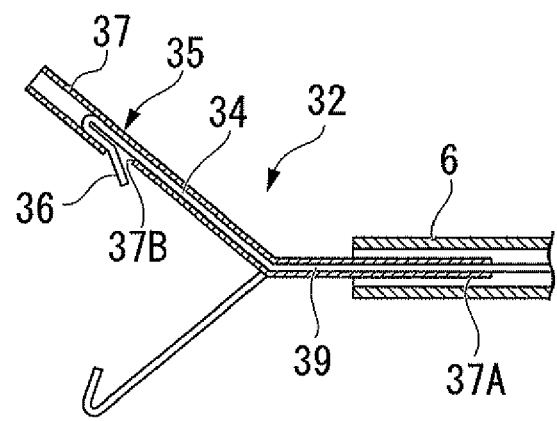
FIG. 7 is a diagram showing a grasping portion in accordance with a modified example of the second embodiment.

Hereinafter, an endoscopic treatment tool 31 in accordance with a second embodiment of the present invention will be described with reference to FIGS. 5 to 7. The endoscopic treatment tool 31 of the present embodiment is different from the endoscopic treatment tool 1 of the first embodiment in that the grasping portion of the present embodiment is constituted by two grasping members and that the pivot portions of the first and second embodiments are different from each other in their shapes. The components that are identical or similar to those of the endoscopic treatment tool 1 of the first embodiment will be denoted by the same reference numeral and repetitious explanations thereof will be omitted.

Figure 5:
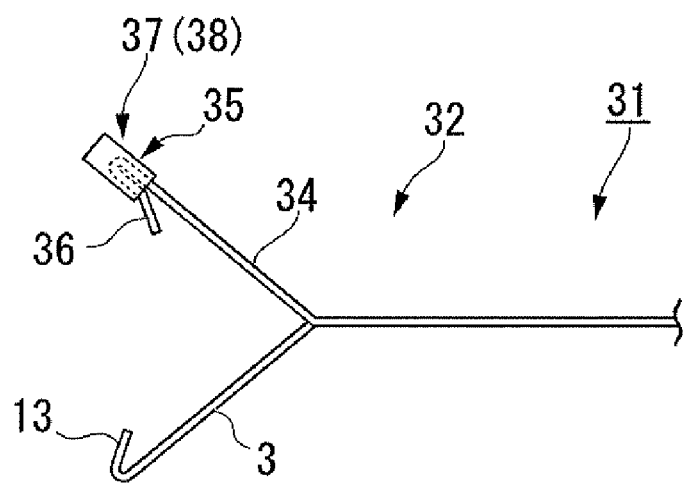
FIG. 5 is an enlarged view of a grasping portion of the endoscopic treatment tool in accordance with a second embodiment of the present invention.

FIG. 5 is an enlarged view of a grasping portion 32 of the endoscopic treatment tool 31 in accordance with the present embodiment. As shown in the exploded diagram of FIG. 6, the grasping portion 32 includes a first grasping member 33 and a second grasping member 10. A first shoulder portion 34 before being processed is longer than the second shoulder portion 3. The first shoulder portion 34 is folded back flat at the position F1 at which the first shoulder portion 34 is about 3 mm longer than a second shoulder portion 3. In this way, a pivot portion 35 is formed at a position F1 so as to protrude in the same direction as the longitudinal direction of the first shoulder portion 34. The folded end portion of the first shoulder portion 34 is folded back again at a position corresponding to about 3 mm after the folded end portion so as to protrude in such a direction that the end portion is substantially opposed to a current-carrying portion 13 of the second shoulder portion 3. In this way, a current-carrying portion 36 is formed. That is, the first grasping member 33 is constituted by the first shoulder portion 34, the pivot portion 35 and the current-carrying portion 36. In addition, the first shoulder portion 34 and the second shoulder portion 3 become to have substantially the same lengths after such a processing (folding).

The pivot portion 35 is capped with a tube 37 that is formed of an insulating material and has heat-shrinkable properties. With the tube 37, an insulating portion 38 is provided to the distal end of the pivot portion 35. Although an end portion of the tube 37 is open, since the end portion of the tube 37 extends out more than 1 mm from the distal end of the pivot portion 35, the tissues in contact with the pivot portion 35 at the time of supplying current thereto are not thermally damaged.

A heat-shrinkable tube is useful for capping the pivot portion 35, but instead of this, a general tube made of resin or the like may be used for insulation of the pivot portion 35.

According to the endoscopic treatment tool 31 of the present embodiment, since the grasping portion 32 can be constructed by two members of the first and second grasping members 33 and 10, it is possible to simplify the structure of the treatment tool. In addition, since a proximal portion 39 of the grasping portion 32 can be made narrower, the grasping portion 32 can be received in a first sheath 6 in a smoother manner.

Furthermore, since the pivot portion 35 is formed by folding back the distal end of the first grasping member 33, tissues are not likely to be damaged when the pivot portion 35 is moved to press against the tissues.

In the present embodiment, the description has been made for the case in which the tube 37 covers only the vicinity of the pivot portion 35. However, instead of this, as shown in the modified example of FIG. 7, the tube 37 may cover the entire surface of the first shoulder portion 34, and the length of the tube 37 may be set such that the end portion 37A of the tube 37 is always disposed in the inside of the first sheath 6. In this case, the current-carrying portion 36 is exposed out from a cutout 37B formed in the tube 37.

In this way, the tube 37 is rarely separated from the pivot portion 35. In addition, when the first sheath 6 is made to move forward so as to allow the grasping portion 32 to be received therein from the side of the proximal portion 39, the end portion 37A rarely collides with the first sheath 6.

Third Embodiment

Figure 9:
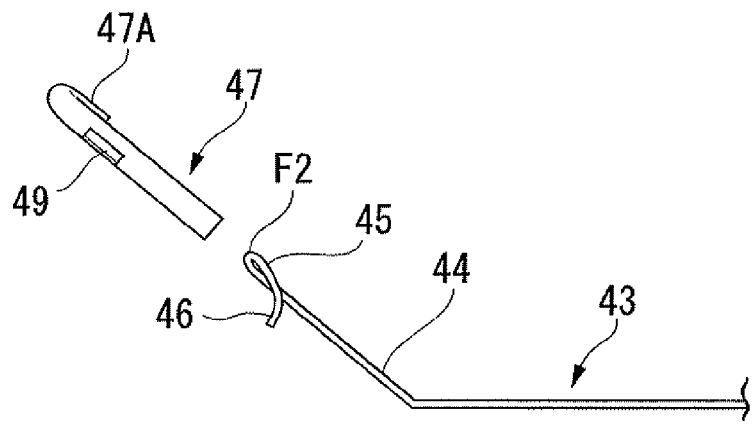
FIG. 9 is an enlarged exploded view of the grasping portion.
Figure 10:
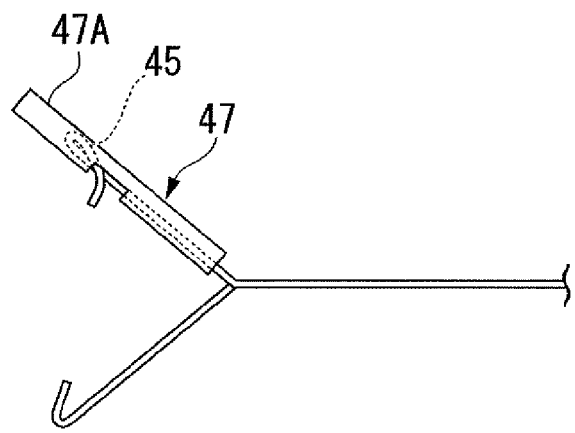
FIG. 10 is a diagram showing a grasping portion in accordance with a modified example of the third embodiment.

Hereinafter, an endoscopic treatment tool 41 in accordance with a third embodiment of the present invention will be described with reference to FIGS. 8 to 10. The endoscopic treatment tool 41 of the present embodiment is different from the endoscopic treatment tool 1 of the first embodiment in that the grasping portion of the present embodiment is constituted by two grasping members and that the pivot portions of the first and third embodiments are different from each other in their shapes. The components that are identical or similar to those of the endoscopic treatment tool 1 of the first embodiment will be denoted by the same reference numeral and repetitious explanations thereof will be omitted.

Figure 8:
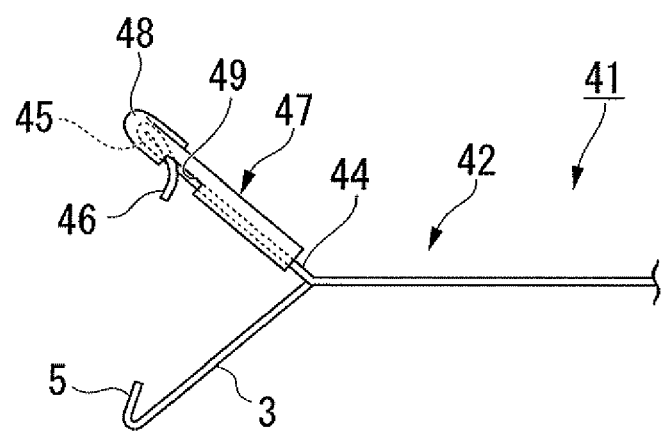
FIG. 8 is an enlarged view of a grasping portion of the endoscopic treatment tool in accordance with a third embodiment of the present invention.

FIG. 8 is an enlarged view of a grasping portion 42 of the endoscopic treatment tool 41 in accordance with the present embodiment. As shown in the exploded diagram of FIG. 9, the grasping portion 42 includes a first grasping member 43 and a second grasping member 10. A first shoulder portion 44 before being processed is longer than a second shoulder portion 3. The first shoulder portion 44 is twistingly folded back at a position F2 at which the first shoulder portion 44 is about 3 mm longer than the second shoulder portion 3. In this way, a pivot portion 45 is formed at the position F2 so as to protrude in the same direction as the longitudinal direction of the first shoulder portion 44. The twisted end portion of the first shoulder portion 44 corresponding to the twisted portion is bent at a position at which the first and second shoulder portions 44 and 3 become to have the same lengths so as to protrude in such a direction that the end portion is substantially opposed to a current-carrying portion 13 of the second shoulder portion 3. In this way, a current-carrying portion 46 is formed.

The first shoulder portion 44 is inserted in a tube 47 formed of an insulating material such as a resin. Substantially the entire surface of the first shoulder portion 44 including the distal end of a pivot portion 45 is covered with the tube 47 and is thus insulated. In this way, an insulating portion 48 is provided to the distal end of the pivot portion 45. In addition, the twisted shape of the pivot portion 45 can be fixed by the tube 47. A cutout 49 is formed in the side surface of the tube 47, and the current-carrying portion 46 is exposed out from the cutout 49. A distal end portion 47A of the tube 47 that extends out from the distal end of the pivot portion 45 is folded back and welded and fixed to the tube 47, whereby the distal end of the pivot portion 45 is completely covered and insulated.

According to the endoscopic treatment tool 41 of the present embodiment, substantially the entirety of the first shoulder portion 44 is insulated by the tube 47. Therefore, it is possible to prevent the first shoulder portion 44 from making contact with tissues adjacent to the target tissue and thus prevent the adjacent tissues from being unintentionally cauterized by the high-frequency current flowing through the first shoulder portion 44.

Since the distal end portion 47A of the tube 47 covering the pivot portion 45 is folded back and fixed to the tube 47, it is possible to insulate the pivot portion 45 in a more secure manner. In addition, it is possible to suppress tissues from being damaged when the pivot portion 45 is moved to press against the tissues.

In the present embodiment, the description has been made for the case in which the distal end portion 47A of the tube 47 is folded back. However, instead of this, as shown in the modified example of FIG. 10, the distal end portion 47A may be configured to extend out a predetermined length from the distal end of the pivot portion 45, thereby insulating the pivot portion 45. In this case, in a manner similar to the second embodiment, the extension length of the distal end portion 47A is preferably set to 1 mm or more.

Fourth Embodiment

Figure 11:
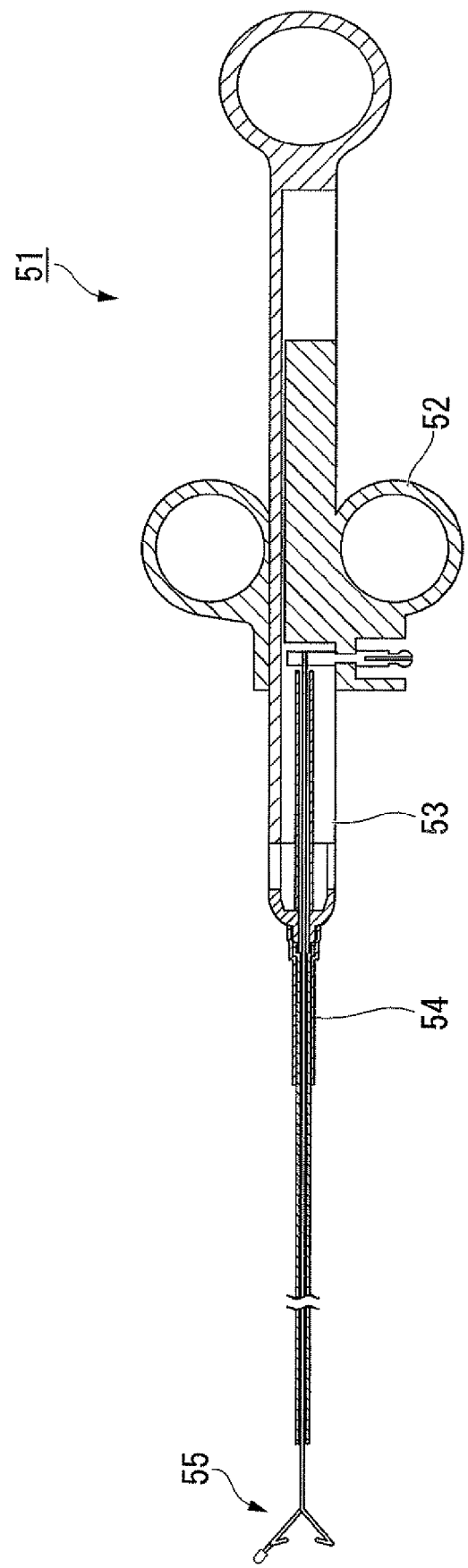
FIG. 11 is a diagram showing an endoscopic treatment tool in accordance with a fourth embodiment of the present invention.

Hereinafter, a fourth embodiment of the present invention will be described with reference to FIG. 11. The endoscopic treatment tool 51 of the present embodiment is different from the endoscopic treatment tool 1 of the first embodiment in that the second sheath is not provided for the present embodiment.

Unlike the sliding portion 8 of the endoscopic treatment tool 1 of the first embodiment, a sliding portion 52 of the endoscopic treatment tool 51 of the present embodiment is not provided with a second sheath 18. Therefore, the outer peripheral surface of a first sheath 6 is not covered except for the portion of the outer peripheral surface of the first sheath 6 connected to a main body 53 which is covered with a protecting tube 54 having a length of about several centimeters, for example. In addition, a grasping portion 55 has the same shape as that of a grasping portion 4 of the endoscopic treatment tool 1.

Since in the endoscopic treatment tool 51 of the present embodiment, the second sheath 18 is not fixed to the sliding portion 52, when closing the grasping portion 55, the sliding portion 52 is pulled forward so as to allow the grasping portion 55 to be retracted toward and thus received in the inside of the first sheath 6.

According to the endoscopic treatment tool 51 of the present embodiment, since the second sheath 18 is not provided, it is possible to provide an endoscopic treatment tool that has a simple structure and can be manufactured in a simple manner.

Hereinabove, although the preferred embodiments of the present invention have been described and illustrated, the present invention is not limited to these embodiments. Additions, omissions, substitutions, and other modifications can be made to the configurations described and illustrated above without departing from the scope and spirit of the present invention.

For example, in the embodiments described above, the description has been made for the case in which the second sheath 18 has the same length as that of the operation channel of the endoscope device. However, as long as the second sheath can be sufficiently fixed by the frictional force acting on the operation channel, the second sheath may be configured in shorter length to extend out only about 10 cm from the forceps plug of the endoscope device. With the adoption of such a configuration, the endoscopic treatment tool can be assembled in a simple manner and can be constructed with a smaller number of components.

Accordingly, it should be noted that the scope of the present invention is to be defined by the claims appended hereto rather than being limited to the descriptions presented above.

What is claimed is:

1. An endoscopic treatment tool, comprising:
    a grasping portion that has a first shoulder portion and a second shoulder portion having substantially the same length as that of the first shoulder portion, the first and second portions being arranged to make a predetermined angle relative to each other;
    a current-carrying portion that protrudes out from a distal end of each of the first and second shoulder portions;

a pivot portion that is disposed in the distal end of the first shoulder portion so as to protrude in substantially the same direction as the longitudinal direction of the first shoulder portion, the distal end of the pivot portion being provided with an insulating portion;

a wire in which a first end portion thereof is connected to the grasping portion;

a sheath which has a tubular shape, and into which the wire and the grasping portion are inserted in a sliding manner;

a main body to which the sheath is fixed; and a sliding portion which is disposed to move in the longitudinal direction of the main body in a sliding manner, and to which is connected a second end portion of the wire.

2. The endoscopic treatment tool according to claim 1, wherein the first shoulder portion, the pivot portion, and the current-carrying portion constitute a single member.

3. The endoscopic treatment tool according to claim 1, wherein the insulating portion is formed of an insulating material and provides insulation to the pivot portion and the first shoulder portion.

4. The endoscopic treatment tool according to claim 1, further comprising an outer sheath that has a tubular shape, and into which the sheath is inserted in a sliding manner, the end portion of the outer sheath being fixed to the sliding portion.

* * * * *

UNITED STATES PATENT AND TRADEMARK OFFICE
CERTIFICATE OF CORRECTION

PATENT NO. : 7,691,104 B2   Page 1 of 1
APPLICATION NO. : 11/880995
DATED : April 6, 2010
INVENTOR(S) : Hironori Yamamoto et al.

It is certified that error appears in the above-identified patent and that said Letters Patent is hereby corrected as shown below:

Title Page should read:
(75) Inventors: Hironori Yamamoto, Shimotsuke (JP); Megumi Kimura, Tokyo (JP);
                  Ichiro Takahashi, Tokyo (JP); Ryoko Yamazaki, Kuroishi (JP);
                  Tatsuya Kaneko, Tokyo, (JP)

Signed and Sealed this

Fifth Day of October, 2010

David J. Kappos
*Director of the United States Patent and Trademark Office*